United States Patent
Koschmieder et al.

[11] Patent Number: 5,943,118
[45] Date of Patent: Aug. 24, 1999

[54] ARRANGEMENT AND METHOD FOR ILLUMINATION IN A STEREOSCOPIC OPHTHALMIC MICROSCOPE

[75] Inventors: Ingo Koschmieder, Jena; Egon Luther, Cospeda; Klaus-Ditmar Voigt, Jena, all of Germany

[73] Assignee: Carl Zeiss Jena GmbH, Jena, Germany

[21] Appl. No.: 09/053,277

[22] Filed: Apr. 1, 1998

[30] Foreign Application Priority Data

Mar. 19, 1998 [DE] Germany ............... 198 12 050

[51] Int. Cl.$^6$ ......................................... A61B 3/02
[52] U.S. Cl. ................................................ 351/243
[58] Field of Search .......................... 351/205, 206, 351/214, 239, 243

[56] References Cited

U.S. PATENT DOCUMENTS

| 4,764,007 | 8/1988 | Task | 351/243 |
| 5,512,966 | 4/1996 | Snook | 351/205 |

*Primary Examiner*—George Manuel
*Attorney, Agent, or Firm*—McAulay Nissen Goldberg Kiel & Hand, LLP

[57] ABSTRACT

Ophthalmic device, such as a slit lamp or a visual acuity testing device or a combination of these devices, for variable illumination of the patient's eye with illumination fields of different geometries, wherein the illumination of the patient's eye is generated by means of chip components which are controllable electronically with respect to their light transparency, light reflection or light emission and which are illuminated by reflected light or transmitted light or are self-illuminating.

22 Claims, 4 Drawing Sheets

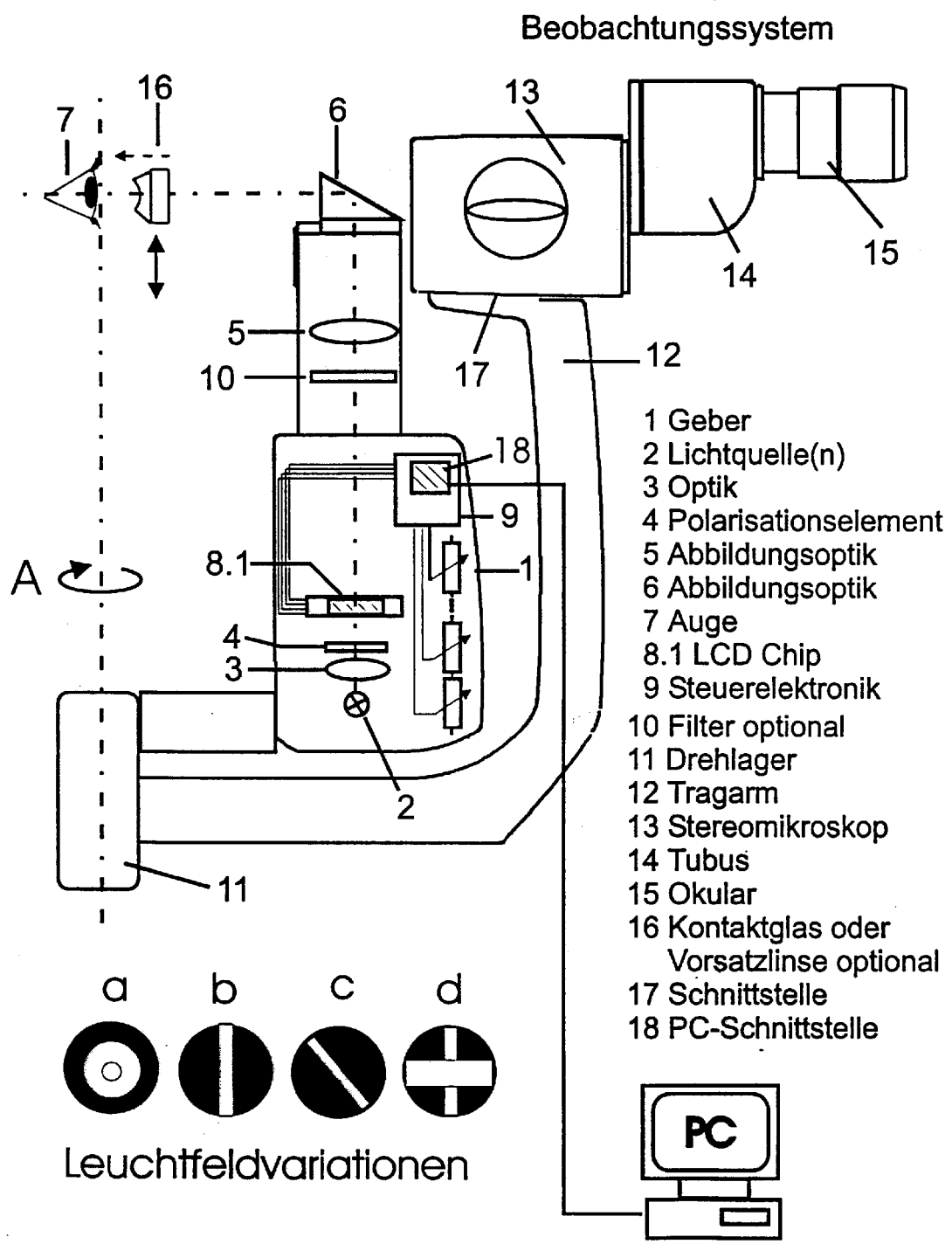

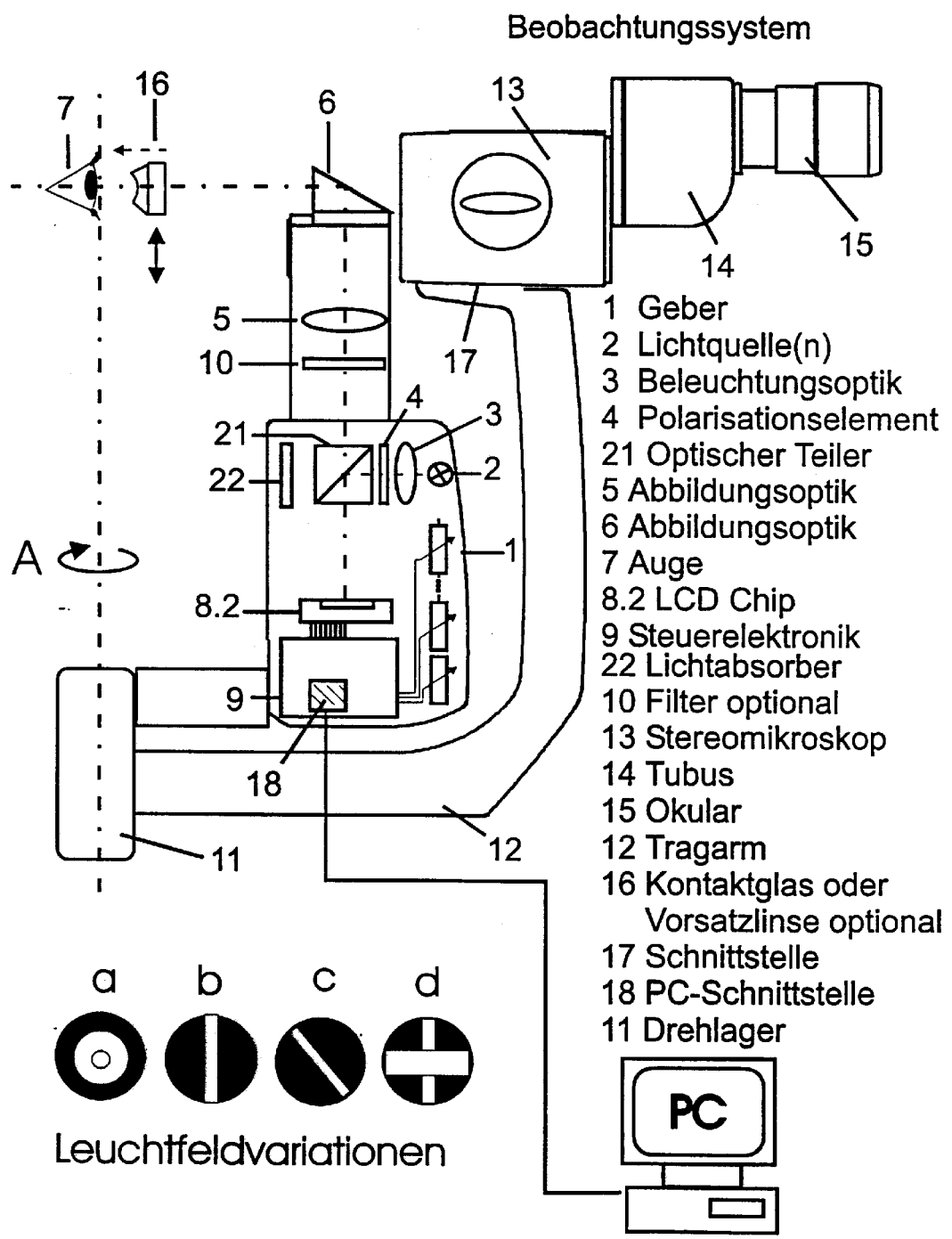

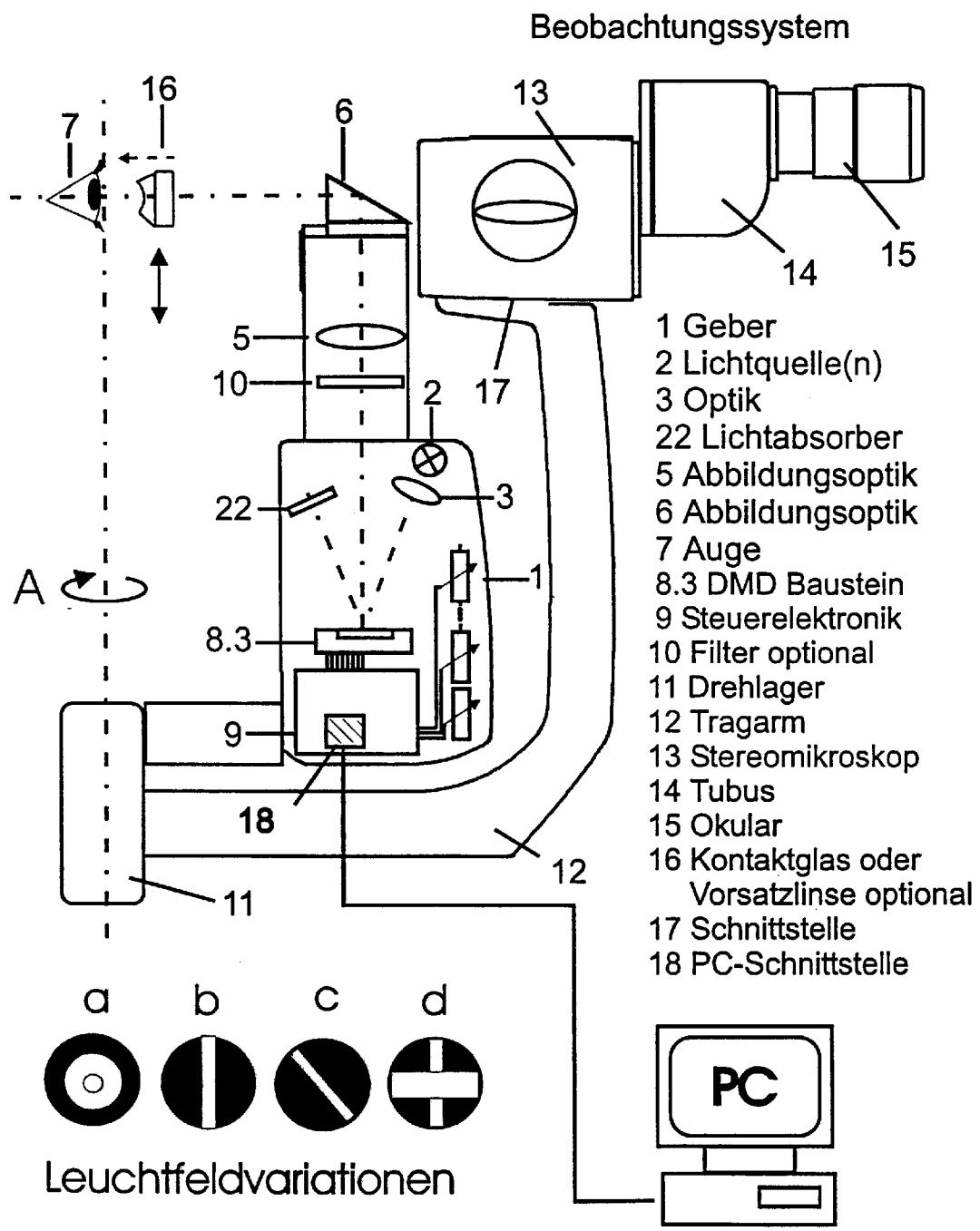
Abb.3

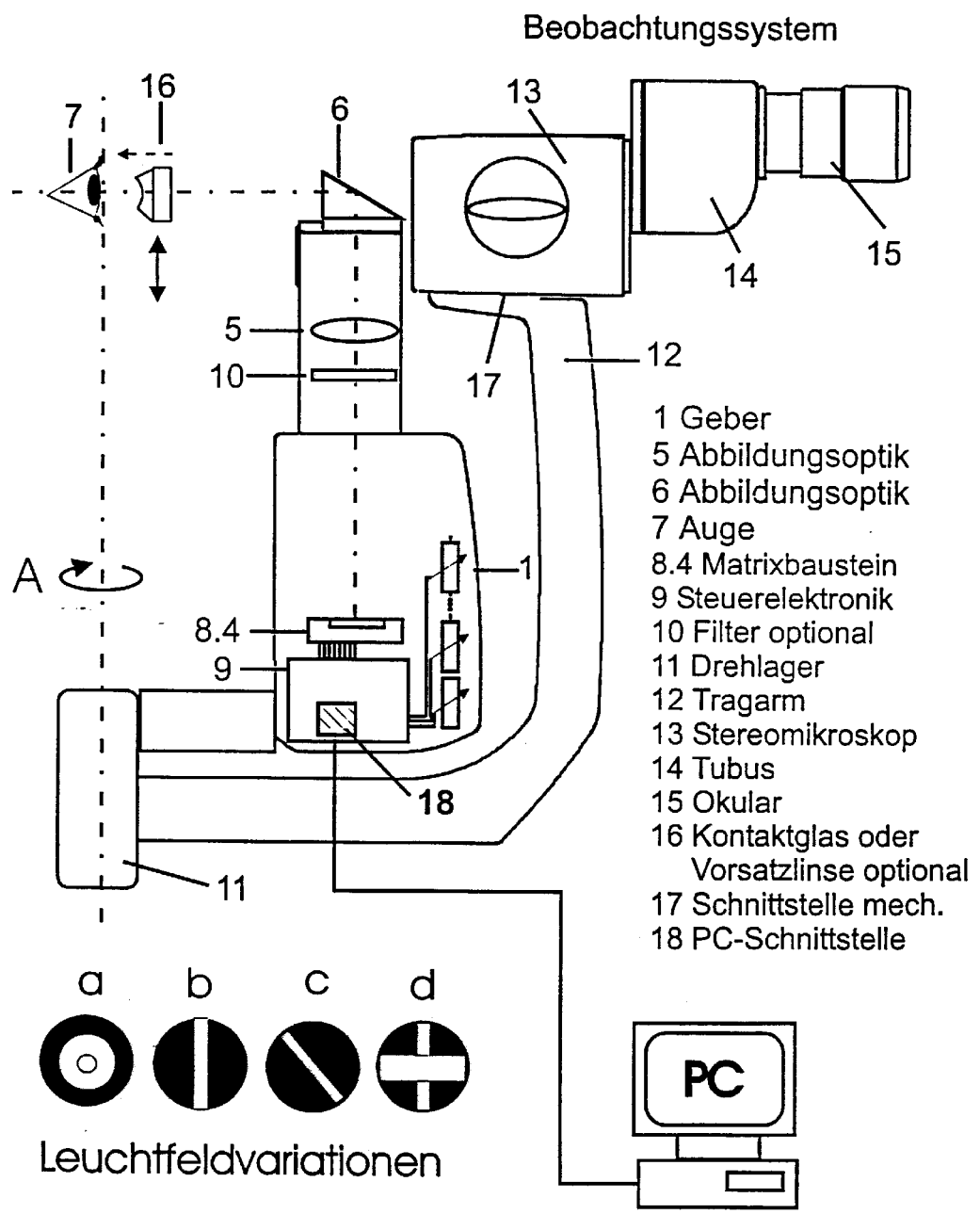

ARRANGEMENT AND METHOD FOR ILLUMINATION IN A STEREOSCOPIC OPHTHALMIC MICROSCOPE

BACKGROUND OF THE INVENTION a) Field of the Invention

In an ophthalmic microscope (e.g., a slit lamp), an illumination arrangement is used for generating changeable illumination fields, illumination colors and illumination intensities in and on the eye. The use of diffuse survey or broad-beam illumination, circular illumination fields with variable diameter, and sharply delimited light slits for generating an optical sectional image through transparent media of the eye is conventional. Formerly, exclusively mechanical/optical elements such as pinhole diaphragms and slit diaphragms, filter glasses, test targets or patterns, etc. were used to change the illumination field geometry.

b) Description of the Related Art

A typical ophthalmic microscope is described in Document No. 311214-7560.145 by Carl Zeiss.

All of the previously known methods and arrangements have faults.

Adjustment of the mechanical component groups is very complicated. The parallelism of the slit edges in the case of a very narrow slit is difficult to guarantee. Thermal expansion of mechanical structural component parts and shaking caused by transporting can necessitate readjustment. The reproducibility of settings for measurement purposes is limited. The arrangement of operating controls is predetermined to a great extent by the mechanical construction and ergonomic concerns cannot always be taken into account in an optimum manner.

The multiplicity of conceivable illumination field geometries is limited by the respective fixed slit diaphragms and pinhole diaphragms. In particular, the possibilities for displaying test patterns are very limited. The space requirement for the illumination device is correspondingly large due to the use of mechanically adjustable component groups for changing the illumination field geometry (drives, displacement elements, diaphragms).

In WO 96/04581, a DMD mirror is used for projection of vision tests.

OBJECT AND SUMMARY OF THE INVENTION

It is the primary object of the invention to simplify the illumination of the patient's eye.

The invention describes arrangements and methods for illuminating the eye in connection with the use of ophthalmologic observation devices. The invention is based on varying the illumination field not by mechanical/optical components as was formerly the case, but rather by special optical/electronic chip components which are in turn capable of generating different illumination field geometries. Controlling and variation are carried out by electronic means. This method bypasses the above-mentioned disadvantages and difficulties in conventional ophthalmologic illumination devices and can deliver constantly reproducible illumination field geometries for a very wide variety of applications.

In particular, the display of strictly parallel slit images, fields for measurement purposes, and self-illuminating test patterns for imaging in and on the patient's eye is made possible. The space requirement for the entire arrangement is reduced and controlling and variation are simplified by electronic measures.

In general, the following variants are suitable for this method:

1. LCD projection by transmitted light method
2. LCD projection by reflected light method
3. DLP projection
4. Self-illuminating chip components such as electroluminescent modules.

BRIEF DESCRIPTION OF THE DRAWINGS

Basic arrangements corresponding to the above-mentioned methods are shown in FIGS. 1 to 4.

Different illumination field variations are shown in within drawing within each sequence as parts a) to d).

DESCRIPTION OF THE PREFERRED EMBODIMENTS

The utilized chip components are known from projection technique and can be used in modified arrangements for producing illumination systems suitable for ophthalmologic purposes.

Prerequisites for use are, in every case, very high resolution (pixel) and a sufficiently high contrast. These prerequisites are met, for example, by components manufactured by DMD (Texas Instruments) and D-ILA (JVC) Technologie.

FIG. 1: LCD Projection by Transmitted Light

A light source 2, illumination optics 3, and a polarizer 4 uniformly and completely illuminate a LCD chip 8.1, e.g., Sony LXC016AL.

By means of transmitter elements 1 which are located in the device or are controllable externally by a PC, the user can make specific changes in the illumination field geometry which reach the chip via the control unit 9, e.g., the illumination field diameter a, as well as dimensioning of a slit b projected on the eye and the slit angle position c or the shape d itself can be correspondingly adjusted.

With respect to d, as has been mentioned, a slit can be generated in two coordinates, but a grid or graticule to be projected can also be generated, for example.

An image of the LCD chip (display) 8.1 can be projected in or on the eye 7 to be tested by means of imaging optics (shown schematically), in this case, an objective 5 and a deflection prism 6.

The brightness of the illumination is regulated by varying the brightness of the light source 2. Special colors can be generated through the use of filters 10 in the beam path.

The patient is protected from harmful radiation loading by filters, shown schematically at 10. The entire illumination device is arranged, together with the observation system 13, 14, 15, on a pivot bearing 11 so as to be pivotable about an axis A. The observation system 13, 14, 15 is swivelable about axis A independent from the illumination.

The observation system 13, 14, 15 is fastened to a support arm 12. As was mentioned, it can include, for example, a stereo microscope 13 with tube 14 and eyepieces 15 for visual observation, or a video camera system with a monitor, or a combination thereof (microscope body with suitable beam splitter for simultaneous visual observation and recording).

The support arm is attached at a mechanical interface 17.

By means of a suitable contact lens (or auxiliary lens) 16 (known method), test patterns which are illuminated in an optional manner or which are self-illuminating can be projected onto the retina of the eye and used to monitor visual acuity in a particularly advantageous manner. The same effect is achieved by modifying the imaging optics 5 in such a way that a) the optics 5 are displaced such that the LCD chip (display) 8.1 is imaged to infinity, or
b) the optics 5 comprise a plurality of individual components, wherein an imaging of the LCD chip (display) 8.1 to infinity is effected by temporarily removing individual components from the beam path.

FIG. 2: LCD Projection by Reflected Light

A light source 2, illumination optics 3, and a polarizer 4 illuminate a LCD chip (display) 8.2 uniformly and completely by means of a special beam splitter 21. Principle: see JVC Video Presentation, Issue March 1997.

In this case, the LCD chip 8.2 is arranged in reflected light in that the illumination light is reflected in laterally and initially reaches the LCD chip 8.2 and then passes through the special beam splitter 21 in the direction of the eye 7.

By means of transmitter elements 1 which are located in the device or are controllable externally by a PC, the user can make specific changes in the illumination field geometry which reach the chip via the control unit 9, e.g., the illumination field diameter a, as well as dimensioning of a slit b projected on the eye and the slit angle position c or the shape d itself can be correspondingly adjusted.

With respect to d, as has been mentioned, a slit can be generated in two coordinates, but a grid to be projected can also be generated, for example.

An image of the LCD chip (display) 8.2 can be projected in or on the eye to be tested by means of imaging optics (shown schematically), in this case, an objective 5 and a deflection prism 6.

The brightness of the illumination is regulated by varying the brightness of the light source 2. Special colors can be generated through the use of filters 10 in the beam path.

The patient is protected from harmful radiation loading by filters, shown schematically at 10. The light absorber 22 damps unnecessary light components and prevents unwanted interfering reflections.

The entire illumination device is arranged, together with the observation system 13, 14, 15, on a pivot bearing 11 so as to be pivotable about an axis A. The observation system 13, 14, 15 is swivelable about axis A independent from the illumination.

The observation system 13, 14, 15 is fastened to a support arm 12. As was mentioned, it can include, for example, a stereo microscope 13 with tube 14 and eyepieces 15 for visual observation, or a video camera system with a monitor, or a combination thereof (microscope body with suitable beam splitter for simultaneous visual observation and recording). The support arm is attached at a mechanical interface 17.

By means of a suitable contact lens (or auxiliary lens) 16 (known method), test patterns which are illuminated in an optional manner or which are self-illuminating can be projected onto the retina of the eye and used to monitor visual acuity in a particularly advantageous manner. The same effect is achieved by modifying the imaging optics 5 in such a way that
a) the optics 5 are displaced such that the LCD chip (display) 8.2 is imaged to infinity, or
b) the optics 5 comprise a plurality of individual components, wherein an imaging of the LCD chip (display) 8.2 to infinity is effected by temporarily removing individual components from the beam path.

FIG. 3: DLP Projection by Reflected Light

A light source 2 and illumination optics 3 uniformly and completely illuminate a DMD chip 8.3 instead of a LCD chip 8.2 in FIG. 2. (Texas Instruments (1996) Product # DLP 007).

By means of transmitter elements 1 which are located in the device or are controllable externally by a PC, the user can make specific changes in the illumination field geometry which reach the chip via the control unit 9, e.g., the illumination field diameter a, as well as dimensioning of a slit b projected on the eye and the slit angle position c or the shape d itself can be correspondingly adjusted.

With respect to d, as has been mentioned, a slit can be generated in two coordinates, but a grid to be projected can also be generated, for example.

An image of the DMD chip (display) 8.3 can be projected in or on the eye to be tested by means of imaging optics (shown schematically), in this case, an objective 5 and a deflection prism 6.

The brightness of the illumination is regulated by varying the brightness of the light source 2. Special colors can be generated through the use of filters 10 in the beam path.

The patient is protected from harmful radiation loading by filters, shown schematically at 10. The light absorber 22 damps unnecessary light components and prevents unwanted interfering reflections.

The entire illumination device is arranged, together with the observation system 13, 14, 15, on a pivot bearing 11 so as to be pivotable about an axis A. The observation system 13, 14, 15 is swivelable about axis A independent from the illumination.

The observation system 13, 14, 15 is fastened to a support arm 12. As was mentioned, it can include, for example, a stereo microscope 13 with tube 14 and eyepieces 15 for visual observation, or a video camera system with a monitor, or a combination thereof (microscope body with suitable beam splitter for simultaneous visual observation and recording). The support arm is attached at a mechanical interface 17.

By means of a suitable contact lens (or auxiliary lens) 16 (known method), test patterns which are illuminated in an optional manner or which are self-illuminating can be projected onto the retina of the eye and used to monitor visual acuity in a particularly advantageous manner. The same effect is achieved by modifying the imaging optics 5 in such a way that
a) the optics 5 are displaced such that the DMD chip (display) 8.3 is imaged to infinity, or
b) the optics 5 comprise a plurality of individual components, wherein an imaging of the DMD chip (display) 8.3 to infinity is effected by temporarily removing individual components from the beam path.

FIG. 4: Self-illuminating Chip Components (for example, electroluminescent miniature screens)

A self-illuminating chip module 8.4 is located in the imaging beam path of the imaging optics 5 and 6.

By means of transmitter elements 1 which are located in the device or are controllable externally by a PC, the user can make specific changes in the illumination field geometry which reach the chip 8.4 via the control unit 9, e.g., the illumination field diameter a, as well as dimensioning of a slit b projected on the eye and the slit angle position c or the shape d itself can be correspondingly adjusted.

With respect to d, as has been mentioned, a slit can be generated in two coordinates, but a grid to be projected can also be generated, for example.

An image of the chip component (display) 8.4 can be projected in or on the eye 7 to be tested by means of imaging optics (shown schematically), in this case, an objective 5 and a deflection prism 6.

The brightness of the illumination is regulated by varying the brightness of the display 8.4 itself. Special colors can be generated by controlling the component 8.4 and/or additionally through the use of filters 10 in the beam path.

The patient is protected from harmful radiation loading by filters, shown schematically at 10. The entire illumination device is arranged, together with the observation system 13, 14, 15, on a pivot bearing 11 so as to be pivotable about an axis A. The observation system 13, 14, 15 is swivelable about axis A independent from the illumination.

The observation system is fastened to a support arm 11. As was mentioned, it can include, for example, a stereo microscope 13 with tube 14 and eyepieces 15 for visual observation, or a video camera system with a monitor, or a combination thereof (microscope body with suitable beam splitter for simultaneous visual observation and recording). The support arm is attached at a mechanical interface 17.

By means of a suitable contact lens (or auxiliary lens) 16 (known method), test patterns which are illuminated in an optional manner or which are self-illuminating can be projected onto the retina of the eye 7 and used to monitor visual acuity in a particularly advantageous manner. The same effect is achieved by modifying the imaging optics 5 in such a way that a) the optics 5 are displaced such that the self-illuminating chip component (display) 8.4 is imaged to infinity, or b) the optics 5 comprise a plurality of individual components, wherein an imaging of the chip component (display) 8.4 to infinity is effected by temporarily removing individual components from the beam path.

As a result of the advantageous constructions of the invention, the possibilities for use of a slit lamp are expanded and a completely novel ophthalmologic combination device is provided for ophthalmologic examination and testing of visual acuity. It is advantageously possible in ophthalmologic examination as well as in visual acuity testing to initiate a pre-programmed, changeable illumination sequence, for example, the above-mentioned slit rotation or alternating optotypes or spectral beam characteristics.

The selected sequence can be adjusted, for example, in the PC and transmitted to the device/input means/control panel via an interface.

The illumination image generated on or in the eye can be recorded parallel with the illumination sequence by means of a video camera and the recordings for adjusted illumination sequences can be stored in the PC, for example, via interface 18 for purposes of comparison or measurement.

For purposes of storage, at least one allocation or cross-reference feature for detecting the adjusted programmed illumination sequence and illuminated eye of the patient is also stored at the same time, so that this illumination sequence can be carried out again subsequently, if need be, on the same eye and the results can be compared.

While the foregoing description and drawings represent the present invention, it will be obvious to those skilled in the art that various changes may be made therein without departing from the true spirit and scope of the present invention.

What is claimed is:

1. An ophthalmic device with slit-shaped illumination of a patient's eye, comprising chip component means for generating the slit-shaped illumination, said chip components being controllable electronically with respect to their light transparency, light reflection or light emission and which are illuminated by one of reflected light and transmitted light and self-illumination.

2. An ophthalmic device for variable illumination of a patient's eye comprising chip component means for providing illumination fields of different geometry, said chip components being controllable electronically with respect to their light transparency, light reflection or light emission and which are illuminated by one of reflected light and transmitted light and self-illumination.

3. A method for the operation of an ophthalmic device according to claim 1 or claim 2, including the steps of initiating and generating an adjusted variable illumination sequence.

4. The method according to claim 3, wherein a recording of the illumination image generated at or in the eye is carried out parallel to the illumination sequence.

5. The method according to claim 4, wherein the recordings for adjusted illumination sequences are stored for purposes of comparison.

6. The method according to claim 5, wherein for purposes of storage, at least one allocation or cross-reference feature for detecting the adjusted illumination sequence and illuminated eye of the patient is stored at the same time.

7. The method according to claim 3, wherein the image information for adjusted illumination sequences is used online or for each recording for purposes of image processing or measurement or is stored.

8. A visual acuity testing device, comprising chip component means for projecting optional test patterns onto the retina, said chip components being controllable electronically with respect to their light transparency, light reflection or light emission and which are illuminated by one of reflected light and transmitted light and self-illumination.

9. A combined ophthalmic examining and visual acuity testing device, comprising chip component means for generating illumination of a patient's eye, said chip components being controllable electronically with respect to their light transparency, light reflection or light emission and which are illuminated by one of reflected light and transmitted light and self-illumination.

10. The ophthalmic device according to claim 1 or claim 2 or claim 8 or claim 9, wherein the illumination of the patient's eye is carried out by at least one LCD component by transmitted light.

11. The ophthalmic device according to claim 1 or claim 2 or claim 8 or claim 9, wherein the illumination of the patient's eye is carried out by at least one LCD component by reflected light.

12. The ophthalmic device according to claim 1 or claim 2 or claim 8 or claim 9, wherein the illumination of the patient's eye is carried out by at least one DMD component by reflected light.

13. The ophthalmic device according to claim 1 or claim 2 or claim 8 or claim 9, wherein the illumination of the patient's eye is carried out by at least one self-illuminating chip component, e.g., electroluminescent chip elements.

14. The ophthalmic device according to claim 1 or claim 2 or claim 8 or claim 9, wherein input means are provided for the user to select the illumination function such as geometry, position or attitude, intensity, spectral composition.

15. The ophthalmic device according to claim 14, wherein the input is effected via a connected PC.

16. The ophthalmic device according to claim 14, wherein the input is effected via a wireless remote control.

17. The ophthalmic device according to claim 14, wherein the input is effected via voice-controlled operation.

18. The ophthalmic device according to claim 1 or claim 2 or claim 8 or claim 9, wherein means are provided for observation and/or image-recording of the illuminated eye of the patient.

19. The ophthalmic device according to claim 1 or claim 2 or claim 8 or claim 9, wherein means are provided for observation and/or image-recording with simultaneous image processing or means are provided for purposes of measurement at or in the illuminated eye of the patient.

20. The ophthalmic device according to claim 1 or claim 2 or claim 8 or claim 9, wherein a rotatable and/or swivelable illumination unit is provided for illumination of the patient's eye.

21. The ophthalmic device according to claim 1 or claim 2 or claim 8 or claim 9, wherein a rotatable and/or swivelable observation/recording unit is provided.

22. The ophthalmic device according to claim 1 or claim 2 or claim 8 or claim 9, which includes an attachment location for selected or combined attachment of observation and/or recording devices.

* * * * *